United States Patent [19]

Menda et al.

[11] 4,000,317
[45] Dec. 28, 1976

[54] ADSORPTION OF SEBUM

[75] Inventors: William Carl Menda, Neshanic; Robert James Mehaffey, River Edge, both of N.J.

[73] Assignee: Colgate-Palmolive Company, New York, N.Y.

[22] Filed: May 6, 1974

[21] Appl. No.: 466,937

Related U.S. Application Data

[63] Continuation of Ser. No. 308,662, Nov. 22, 1972, abandoned, which is a continuation of Ser. No. 26,063, April 6, 1970, abandoned.

[52] U.S. Cl. .............................. 424/357; 424/69; 424/127; 424/347; 424/356
[51] Int. Cl.$^2$ ............... A61K 7/035; A61K 31/015; A61K 33/00; A61K 47/00
[58] Field of Search ............ 424/127, 357, 69, 347, 424/356

[56] References Cited
FOREIGN PATENTS OR APPLICATIONS 7,824  1907  United Kingdom ................ 424/69

OTHER PUBLICATIONS

Cabot, "Cab-O-Sel", (1955) Published by Godfrey L. Cabot Inc., Boston Mass., 7 pages.

*Primary Examiner*—Stanley J. Friedman
*Attorney, Agent, or Firm*—Herbert S. Sylvester; Murray M. Grill; Norman Blumenkopf

[57] ABSTRACT

Sebum, the oily material secreted by the sebaceous glands, especially on the human face, is adsorbed by a thin layer of a pyrogenic colloidal silica of spherical shape and very small particle size. The pyrogenic colloidal silica has a high capacity for adsorbing the sebum and preventing it from exerting its oily effects on the skin. Free flow of sebum from the sebaceous gland is allowed but even in the cases of persons whose sebaceous glands are overactive, the skin is not excessively oily, due to the adsorption effects of the pyrogenic colloidal silica. The appearance of the facial skin of a user is improved, the surface of the skin is less apt to support harmful bacterial and fungal growth and, if make-ups containing dyes or pigments are employed, they are less apt to undergo color changes, due to the effects of oil thereon.

Compositions that may be employed to apply the pyrogenic colloidal silica to the skin are non-oily, aqueous, alcoholic or aqueous alcoholic suspensions of the pyrogenic colloidal silica in certain ranges of concentrations thereof, which may include minor proportions of non-oily adjuvants, such as thickeners, solvents, emollients, pH modifiers, bactericides, drying agents and exfoliants.

By use of a small amount of such a composition, sebum adsorption can be effected over daytime periods of from 4 to 12 hours, with no re-application required and the pyrogenic colloidal silica composition can be used in such small quantities as to be essentially invisible on the skin. Heavier applications may be employed overnight, when unobtrusiveness of the product is not as important.

2 Claims, No Drawings

ADSORPTION OF SEBUM

This is a continuation of application Ser. No. 308,662 filed Nov. 22, 1972 which in turn is a continuation of application Ser. No. 26,063 filed Apr. 6, 1970 now both abandoned.

This invention relates to methods and compositions to delay or inhibit the development of oiliness on the human skin, due to secretions of sebum.

The sebaceous glands, located under the skin near hair follicles, secrete a greasy or oily substance known as sebum, which normally flows through the sebaceous duct and into the hair follicle and from there to the surface of the skin, where it is useful to lubricate the skin and the hair thereon. The production of sebum is connected with the process of growth and reproduction of the glandular cells. The sebum is formed in this process and flows continually because the glands are always active. In humans, the largest sebaceous glands and those which secret sebum at the greatest rate are located on the face, scalp and back. Of these the most important are those under the facial skin, principally because they affect the appearance of the person most noticeably. When the sebaceous glands operate to secrete the desired amount of sebum, the skin appears fresh and alive, with a suppleness and healthy glow. When too little sebum flows, the skin becomes dry and tends to crack and wrinkle. When too much sebum is secreted, a characteristic greasy appearance of the skin is observed, which is even more objectionable than dry skin in many instances. Excessively oily skin is a problem associated with adolescence and can result in acne, in which the duct of the follicular canal is hyperkeratinized, leading to the creating of sacs plugged with liquids and solids. These appear as open comedos (blackheads) or closed comedos (whiteheads). The latter, upon rupturing into the dermis excite follicles focal inflammation and cause the production of the reddish-purple lumps characteristic of acne. In addition to the undesirable nature of the oily film on the skin, it has an adverse effect on the appearance of women's cosmetics and make-up, often causing them to change color or shade, due to solubilizing or "wetting" of cosmetic ingredients, especially dyes and pigments.

It appears that skin problems, such as acne and the development of pimples on the face are due to excessive secretions of sebum, which, when incapable of being removed from the follicular ducts, cause inflammations therein. Thus, it would appear to be highly desirable to be able to promote the flow of sebum through the duct. On the other hand, the appearance of excess oil on the skin is undesirable cosmetically. What is needed is a means for allowing free flow of sebum to the skin surface which will, at the same time, counteract the oily appearance of the skin that would normally be the result of such sebum flow. The means for accomplishing these effects should not in themselves create additional problems, such as caking with sebum, blocking of the pores, skin irritation or unsightly appearance and should not be difficult to apply or otherwise employ. Now, in accordance with the present invention, methods and compositions are provided for the treatment of the human skin, especially facial skin, whereby the oiliness of the skin, characteristic of excessive secretions of sebum, is easily corrected by simple methods, employing inexpensive and stable compositions, while at the same time sebum flow is not inhibited.

In accordance with the present invention, a method for slowing development of excessive oiliness on the skin comprises applying to the skin, which would otherwise become excessively oily, a non-oily aqueous, alcoholic or aqueous alcoholic suspension of pyrogenic colloidal silica. The silica suspension applied is preferably employed as an aqueous alcoholic suspension which may contain adjuvants such as thickeners, exfolinats, bactericides, etc., and in which the pyrogenic colloidal silica is substantially all in the form of particles which are ultimately spherical in shape and within the 2 to 20 millimicron diameter range. Also within the invention are thickened aqeuous alcoholic suspensions of such pyrogenic colloidal silica, useful in the described method.

The pyrogenic colloidal silica used in the methods and compositions of this invention is a very special type of adsorbent powder. Due to the method of manufacture, by a vapor phase process in which silicon tetrachloride is hydrolyzed at 1,000° C., the silica is produced as very small, uniformly sized particles. The ultimate particle shape is spherical and the particle size is smaller than the particles in common smokes. However, the particles do tend to link together, sometimes in solvent media, and such linking or clumping is a factor in producing a thickening action which has been noted in some liquids. By applying shear forces or by other mechanical or physical means, the ultimate particle size of the silica may be reached. This is from 2 to 20 millimicrons, corresponding to the diameters of the spheres. Substantially all the particles, usually at least 90%, generally more than 95% and preferably more than 99.5% thereof, are of diameters within the mentioned range. Usually the bulk of the particles of any particular average size is within 6 millimicrons of that average size. Although it is possible to make fumed silicas of various other particle sizes, such as those averaging up to about 50 millimicrons in diameter, such larger particles are considered to be unsuitable for the present adsorptive purposes.

Methods for the manufacture of pyrogenic silicas of the types employed in the present composition may be found in the U.S. Pat. Nos. 2,886,414 and 3,391,997. Commercially, the present products are available under the tradename Cab-O-Sil and are produced by Cabot Corporation, Boston, Mass. Specifically, Cab-O-Sil M-5 has an average particle diameter of about 11 millimicrons, whereas the corresponding H-5 grade has a smaller average particle diameter, being about 7 millimicrons. The surface areas of the pyrogenic colloidal silicas are exceedingly large and it is a combination of this factor, with the small and uniform particle size and shape, which is considered to contribute significantly to the special adsorptive, hiding and lubricating effects obtained with the present silicas. Surface areas, in square meters per gram, range from about 50 to 450, usually being from 200 to 400. The silicas described are comparatively light, with densities very much lower than those of water and oils, including sebum. Such dersities are ordinarily from about 2 to 2.5 lbs. per cubic foot. The temporary chain structures formed between the particles, mentioned previously, are also considered to contribute significantly to the special properties of the pyrogenic silicas. Among such properties, perhaps the most important in the present application is the high adsorptive effect on various liquids, including sebum moisture and perspiration, and the holding power exerted on such materials, whereby they are held to the pyrogenic silica without being objectionably noticeable.

Because the pyrogenic silicas are of such fine particle size and of spherical shape, they are readily applied to the skin, exhibit a desirable lubricity and avoid scatching or irritation of the skin. Sebum adsorption characteristics and the ability to adsorb perspiration, despite the continuing flow of such materials from the pores of the skin, may be to the extent of 100 to 200% and sometimes, even more, of the weight of the pyrogenic silica itself. In some cases it is considered that a 50% adsorption is readily attainable and the amount of pyrogenic silica to be applied may be calculated safely on this basis. Of course, when pyrogenic silicas other than the types specifically named previously are used, adsorption effects may be different and the amount employed will be changed accordingly. Instead of the particular pyrogenic silicas mentioned, equivalent materials of the same shape, particle size and other characteristics may be used. Thus, colloidal silicas indentified as Quso silicas, made by the Philadelphia Quartz Company, may be employed in partial replacement of the present pyrogenic silicas, providing that particle sizes, size distributions and other properties are similar.

The medium in which the pyrogenic colloidal silica is suspended may be aqueous, alcoholic or aqueous alcoholic. Such a medium is employed to disperse the silica and make it readily and separately applicable to the skin. Although the medium may be in either solid or liquid form, it is generally preferred to employ liquid suspensions of these silicas. When used, the solids will become fluid upon rubbing into the skin and will effectively spread the silica particles evenly over the skin surface. Such solids are preferably gels, pastes or of other similar forms, wherein a substantial proportion of solvent material is present to facilitate application.

The water that is used may be any clean tap water and is preferably low in hardness and dissolved solids contents, preferably containing less than 150 parts per million of such materials. Deionized or distilled waters may be used. The alcohols that are used are preferably the lower monohydric alcohols, although a portion of the alcoholic content may be furnished bt dihydric and polyhydric alcohols. Such proportion should be only minor with respect to the total alcohol content of the preparations employed. The monohydric alcohols that are used include ethanol, isopropanol, n-butanol, isobutanol or t-butanol. In most instances, the alcohol employed will be either ethanol or isopropanol and it is highly preferred, for reasons of safety, odor, volatility, purity and expense, to use only ethanol. Nevertheless, preparations which comprise a major proportions of ethanol and minor proportions of other monohydric alcohols are usable. In some cases, very small quantitites, usually less than 5%, of higher alcohols, having carbon contents as high as 12 carbon atoms per molecule, may be used. The dihydric alcohols that are employable to a minor extent, usually no more than 10% of the alcohol content present being dihydric alcohol(s), are preferably those of 2 to 4 carbon atoms per molecule, of which the most preferred are ethylene glycol and propylene glycol. Of the polyhydric alcohols, a referred example is glycerol, although various other alkane triols, of up to 6 carbon atoms per molecule are useful. In addition to the hydrocarbyl-based alcohols, those comprising intermediate oxygen atoms, such as the polyoxyethylene glycols, triols and polyols may be used to a minor extent, as may be the polylower alkylene diols and polyols, such as polyethylene glycols. Such materials preferably comprise from 2 to 4 carbon atoms in repeating moieties and have a total of no more than 20 carbon atoms per molecule. They will usually contain from 3 to 10 hydroxyls per molecule.

The various alcohols employed are typically used in their normal commerical forms. For example, where desirable, they may contain small proportions of preservatives or anti-oxidants and, in the case of ethanol, may be denatured with the usual denaturing chemicals, e.g., brucine. A preferred denatured ethanol to be employed is that designated SD 40.

The aqueous alcoholic solvent media that are useful will normally contain between 15 to 85% alcohol and 20 to 70% water, on a total composition basis. Thus, the proportion of alcohol to water will usually be within the approximate range of 1/3 to 3/1. Preferably, the proportion of these materials will be within the range of 1/2 to 2/1. Although presence of alcohol is highly desirable in these products, in some circumstances it may be omitted and a composition based only on water may be employed. Such an alcohol-free composition may be suitable for winter use or in hot dry climates, where the volatility contributed to the preparations by the presence of the alcohol is not required and sometimes is undesirable. Usually however, alcohol is an important constituent of the present product because it does aid the water in spreading out the pyrogenic colloidal silica over the skin to which it is applied, forming a uniform layer thereon, and helps to evaporate off the solvent quickly and pleasantly, leaving the skin desirably dry soon after application. It also aids in wetting some of the sebum that may be on the surface of the skin or in the follicular ducts. Thereby, it promotes contact of sebum with the silica and aids in the flow of sebum through the ducts, helping to prevent blockages. In the proportions recited, it assists in maintaining the pyrogenic colloidal silica in dispersion and solubilizes various constituents of the product which may be present, such as some of the exfoliating agents, bactericides and non-oily perfumes. At least 5% of ethanol is preferably used.

Although the pyrogenic colloidal silicas and other inorganic thickeners, such as the colloidal silicates, possess the property of increasing the apparent viscosity of suspensions thereof, probably due to polymeric chain formation, it has been found desirable to use an organic gum, in addition to the inorganic silica, to maintain more homogeneous suspensions of the silica. Such gums, employed in very small proportions, help stabilize the suspensions, making the application of the silica more uniform, and after application, tend to prevent chalking or powdering of the silica and accidental removal of it from the skin. This is especially important in the early stages, after application, when the skin, if previously washed, has not become sufficiently oily to have the silica particles adhere strongly to it. Among the gums or hydrocolloids that are most preferably employed are the carboxymethyl celluloses, the hydroxyalkyl celluloses, the carboxypolymethylenes and the various natural gums. However, various other thickening agents than those specifically named may also be employed, including polyvinylpyrrolidone, various acrylates, vegetable proteins, starch derivatives, gelatins, polyacrylaces and dextrins. The natural gums used include karaya, tragacants, gum acacia, algins, agar agar, pectin, carrageenan, guar, locust bean gum, Irish moss extractives and various derivatives thereof.

The celluloses include the various ethers or esters such as methyl cellulose, methyl ethyl cellulose, sodium carboxymethyl cellulose, sodium carboxymethyl hydroxyethyl cellulose, hydroxyethyl cellulose, ethyl hydroxyethyl cellulose, hydroxypropyl methyl cellulose, hydroxyethyl n-butyl cellulose, hydroxyethyl n-hexyl cellulose, and hydroxyethyl benzyl cellulose. The starches, such as hydroxyethyl starch, alkali metal starch phosphates, carboxymethyl starch, and similar materials may be used. When alcohol is employed in the present compositions, care should be taken so that the gum or other organic thickener used is compatible with the alcohol.

Among the synthetic materials that are most interesting are polyvinyl alcohol, polyvinyl pyrrolidone, vinyl pyrrolidone copolymers and what may be characterized as carboxyvinyl polymers, e.g., Carbopol 934. The various synthetic and natural organic gums and thickeners are described at length in *The Chemistry and Manufacture of Cosmetics*, Vol. II, Second Edition, by Haison G. DeNavarre (D. Van Nostrand Company, Inc., 1962), pages 109–154.

Inorganic thickening agents, which may be employed in small quantities to supplement the organic thickeners in the present compositions include various silicates, such as hydrated aluminum silicates, zeolites, magnesium aluminum silicates, lithium silicate, zirconium silicate, calcium silicate and magnesium silicate, which are obtainable by chemical reactions or may be found in natural condition in the earth. Such materials, of which bentonite and veegum are representative, when ground fine, perform a thickening function similar to that obtained from the present pyrogenic colloidal silicas. A detailed listing of the various hydrous silicates and other inorganic silicates which function as thickening agents may be found in *The Chemistry and Manufacture of Cosmetics*, Vol. II, pages 49–59.

The exfoliant materials which are useful in the present compositions because they tend to remove dead skin scales and other unwanted solid materials from the skin include those chemicals known for this purpose. Perhaps the best of these is sulfur but also useful are resorcinol, salicylic acid, etc. Such materials, in addition to removing dead skin, also tend to have a drying effect on the skin and thereby counteract oiliness.

Various bactericides useful in cosmetics are applicable for the skin-treating purposes of the present invention. Thus, hexachlorophene, halosalicylanilides, trichlorocarbanilide and quarternary ammonium salts such as benzalkonium halides, cetyl trimethyl ammonium bromide and dimethyl dibenzyl ammonium chloride, and various other of the phenolics, halogenated phenolics or sulfur-containing phenolics, amides and anilides may be used. Preferably, these will have a certain substantivity to the skin so that their anti-bacterial effect continues after removal of the rest of the pyrogenic silica preparation. Use of bactericides and fungicides in minor proportions helps to maintain the purity of these suspensions during storage and exerts their desirable effect on the skin upon use.

In addition to so-called active ingredients, the present compositions may also contain various adjuvents for other purposes. Of principal importance among these is perfume. Any suitable perfume can be employed in the present products, providing that it is not oily. Of course, it is also important to use perfumes in small quantities so that they will not be adsorbed by the pyrogenic silica to the significant detriment of sebum adsorption. The non-oily perfume ingredients are known to those of skill in the art. They are those materials which do not possess a characteristic fattiness or oiliness found in the higher fatty acid triglycerides and the higher fatty alkanes. Various suitable perfume materials are described in detail in *The Chemistry and Manufacture of Cosmetics*, Vol. I, pages 172–240 and throughout *Perfume, Cosmetics and Soaps*, Sixth Edition, Vol. I, by W. A. Poucher (D. Van Nostrand Company Inc., 1959).

Among other adjuvants that may be employed are coloring agents, such as the ordinary dyes and pigments conventionally utilized in cosmetics. A listing of such dyes, suitable for use in cosmetics, is available from the *Food and Drug Administration*. Various pigments are listed in a text, *Perfumes, Cosmetics and Soaps*, by W. A. Poucher, at Vol. I, pages 347–350. In some cases it may be desirable to employ those pigments or dyes which are known as fluorescent materials or ultraviolet absorbers, which often emit light which causes a desired brightening effect on the skin when there impinges thereon radiation convertible to the fluoresced wave length.

The present compositions and methods utilize non-oily materials because the presence, to any significant extent, of oily constituents such as fats, higher fatty acids, greases, petrolatum, higher fatty acid amides, alkylolamides, and glycerides, impedes the adsorption of sebum by the pyrogenic colloidal silica. Since adsorption of the sebum is important in preventing an oily appearance of the skin and in moving of the sebum through the sebaceous and follicular ducts to the skin surfaces, to prevent blockages from occurring in such ducts, the presence of oily materials in the compositions applied is to be avoided. According to a recent analysis of sebum, it comprises about 5% squalene, 25% of triglycerides, 20% free unsaturated fatty acids and 10% of free saturated fatty acids. It also contains a small percentage of free cholesterol, usually, from 0.6 to 2.4% and a total cholesterol content of about 2 to 5 ½%. The melting point of sebum is 35–36° C. and its hydrocarbon content is about 10 to 15%. Its acid number is 63–73 and iodine number is 61.5–62.5. From the above analysis, it is seen that although there are differences between sebum and ordinary fatty oils, the similarities make it evident that the present compositions should be non-oily in order to avoid preferential adsorption by the silica of composition constituents, rather than of the sebum.

Because of the undesirability of using oily materials in the present compositions, some of the commonly employed emollients are to be avoided. However, oily materials such as the glycerides and higher fatty alcohols and acids can be replaced by polyhydric alcohols such as glycerol, sorbitol and polyethylene glycols, which exert emollient and humectant effects. Similarly, other non-oily emollients and humectants may be included in the present compositions in small proportions.

The present compositions will usually have a slightly acidic pH, approximating that of the skin. Generally, this will be between 4 and 6, although in some instances a pH as low as 3 may be usable and even pH's as high as 9 are sometimes acceptable in particular applications, especially where the skin is more strongly acidic than usual. Generally however, the pH of the present preparations will be between 3 and 7, preferably between 4 and 6. Usually the pH of the adsorbent composition is determined by the joint effect of the various components. In some circumstances acids, bases, buffering agents or other conventional pH-modifying materials may be added to regulate the pH so that it is within the described range.

In the invented compositions, the pyrogenic colloidal silica is a minor component, with the solvent medium being the major component. Although proportions of colloidal silica as high as 25% can be employed and in some situations greater proportions are usable, generally the pyrogenic colloidal silica comprises from 1.5 to 10% of the liquid or solid composition. When less than 1.5% is employed adsorptive power of the product is diminished and when less than 0.5% is used it is generally considered that the adsorption characteristics are lowered so much as to require the use of an excessive amount of the product, which would wet the skin too much and make the liquid preparation undesirable to employ. Thus, although the amount of pyrogenic colloidal silica can be modified by employing more or less of the suspensions of the invention, as a practical matter the lower limit of silica content in the product is 0.5% and preferably is 1.5%. Within the range of 1.5 to 10%, it is preferred to use compositions containing less colloidal silica for daytime application and to reserve those having greater proportions of the special adsorbent for nighttime use. This is because the compositions containing more silica are more noticeable when used, which is less objectionable at night than in the daytime. For daytime use, from 1.5 to 3% silica compositions are employed and at night from 3 to 10% silica compositions are preferred. The silica used, although it contains very small proportions of other materials, such as water, inorganic salt and metal oxides, is usually at least 95% pure and is generally of 98% or greater purity. Accordingly, it may be considered to be pure silica for the purpose of calculations of the proportions to be employed.

Water, which is an important component of the invented compositions, whether they are in liquid or solid form (in the latter case with the compositions usually being thickened to a gel or paste), comprises from 5 to 98%, preferably from 20 to 70% and most preferably from 30 to 60% of the composition. The alcohol present, usually ethanol, is from 0 to 90%, preferably 25 to 75% and most preferably from 30 to 60%, on a total composition basis. Relative proportions of alcohol and water were previously given.

The exfoliating agent employed will be a very small proportion of the composition, usually being from 0 to 3% thereof, preferably from 0.2 to 3% and most preferably, from 0.5 to 2%. Similarly, bactericides and fungicides comprise from 0 to 2% and usually from 0.1 to 1 or 2% of the product. Although perfume and coloring agents are used in sufficient quantities to obtain desired odorant or appearance effects, normally from 0 to 2% of the non-oily perfume will be employed, with a preferred proportion being from 0.1 to 1.5% of perfume. From 0.0001 to 0.006% and preferably from 0.001 to 0.003% dye, pigment or combination thereof will be used. If employed, emollients, humectants or excipients will generally be present in proportions from 0.5 to 5%, preferably from 0.5 to 2%. Compositions added to modify pH, such as boric acid, monosodium phosphate, gluconates or other suitable pH modifiers, may be used in small quantities, e.g., from 0.1 to 2%, preferably from 0.1 to 1%.

It is not necessary to use any other thickening agent than the pyrogenic colloidal silica but it is generally desirable to employ an organic thickener or gelling material to improve the suspension of the silica in the solvent or dispersing medium and additionally, to contribute a binding, suspending and leveling effect on the dispersion during storage and use. The proportion of thickener, preferably of the organic type, is generally from 0 to 10% of the composition, preferably from 0.2 to 5% and most preferably from 1 to 3% thereof. In addition to the organic gum or thickener there may be employed inorganic materials, such as clays or silicates which, because of their small sizes and particular structures, also contribute thickening properties. Such clays, including bentonite and silicates are generally employed in proportions from 0 to 4%, preferably from 0.2 to 3%. It is generally most preferred to have about 1 to 2% of such material present, when it is being used.

The adsorbing compositions may be prepared in various suitable manners. For example, if a thickening material is being used, it may be blended into the solvent medium, sometimes at an elevated temperature, and the other constituents may be added, followed by the pyrogenic colloidal silica. The batch may be stirred with ordinary stirring means or may be homogenized or size-reduced, utilizing conventional mixing, shearing or dispersing equipment. If some of the components are difficulty soluble, they may be initially dissolved in the alcohol or water and the rest of the materials may be blended into the solution, generally following the procedure mentioned above. It is not considered that the various steps in the method for producing these compositions are critical nor is the order of addition of materials vital to the success of the composition. However, it is much preferred that the silica should be dispersed in the solvent medium before having applied to it any concentrated liquid materials other than water and lower alcohols. It is especially important that any material which might be occluded or adsorbed onto the surface of the pyrogenic colloidal silica should not be allowed to contact it until after initial contact with the solvent. It is possible that subsequent contact with the solvent will remove any adsorbed compounds and allow efficient use of the composition for the purpose intended to produce a good product but such an effect should not be relied upon.

In use, the development of excessively oily skin, such as that of the human face, is slowed or inhibited by application to such a skin, which normally would become excessively oily, of a non-oily, aqueous, alcoholic or aqueous alcoholic suspension of pyrogenic colloidal silica. Preferably, such a suspension is a composition of the type previously described. The rate of application to the skin surface in such as to deposit thereon a substantially uniform layer of the silica, usually containing from $5 \times 10^{-5}$ to $10^{-2}$ grams silica per square centimeter of skin surface. In accordance with the previous description, the heavier rates of such application would normally be applied at bedtime so that the pyrogenic colloidal silica deposited would be active all night long, aiding sebum flow to the face through the sebaceous ducts and yet, would prevent the skin from becoming excessively oily. The lighter applications, such as from $5 \times 10^{-5}$ to $2 \times 10^{-3}$ grams per square centimeter of silica are suitable for daytime use, when they have the desirable effect of adsorbing sebum and promoting its flow, while at the same time not being so obtrusively present as to undesirably affect the user's appearance.

Of course, when the adsorbent composition is "saturated" with sebum, it should desirably be washed off and a new application should be made. Usually this will not be necessary for at least 4 hours after application, even in this case of heavy sebum-excreting skin, because of the high adsorbing power of the silica. In most cases, if the correct proportion of silica suspension has been used to adsorb the sebum as it is excreted, the powder may be left on for more than 4 hours and often for up to 12 hours, even with the light daytime application, and the skin will not become excessively oily. Experimental data indicate that persons having oily facial skin excrete from 0.3 to 0.5 milligrams of lipid per square centimeter per 4 hour period, or about 0.1 milligrams per square centimeter per hour. Persons with average skin excrete a little more than half of this amount. Since the pyrogenic colloidal silica can adsorb up to twice its weight of lipid or sebum the application rates given suffice to hold the sebum produced, plus small proportions of perspiration or moisture. With respect to perspiration, since, unlike the sebum, it continually evaporates, the appearance thereof on the skin will not require immediate washing off of the adsorbent because evaporation will often soon remove the perspiration. Although the solids content of the perspiration may interfere somewhat with the activity of the sebum adsorbent, usually this detrimental effect is not insuperable.

The present adsorbents, comprising dispersed pyrogenic colloidal silica of the mentioned particle sizes, are applied to the skin by any suitable means. Generally, liquid suspensions are smoothed on by the fingers or hands. When proportions of thickening agents employed are sufficient to solidify the solvent medium, they may be spread over the face as a solid, gel, paste or lotion, which is then broken down into liquid or film form by rubbing with the fingers. In some circumstances, pressurized sprays or pressure dispensers may be employed to discharge small droplets or liquid streams of the product but the expense of such packaging is not usually warranted by any increase in convenience. The rate of application is such as to be desirably unobtrusive in the daytime or to furnish a base for cosmetic application. By experience, it is soon established what is the best amount of adsorbent preparation to use under given conditions.

After application of a uniform layer of pyrogenic colloidal silica adsorbent to the skin, regular make-up may be applied over it, preferably to an extent which will not interfere with sebum adsorption. In other words, heavy make-up application should be avoided, especially when the make-up includes significant proportions of oily materials.

Before application of the adsorbent composition the face should be washed clean with a mild synthetic detergent or, when acceptable, a soap. It is preferred to apply the adsorbent at room temperature to the skin at normal skin temperature. Thus, there is no need to heat the face or cool it before application. After a period of 4 too 12 hours, when the skin appears to be showing signs of oiliness, due to the sebum no longer being sufficiently adsorbed by the pyrogenic colloidal silica, the adsorbent and any covering make-up should be removed. This can be effected with water alone, in those cases where no make-up is employed and sometimes even in such circumstances. The water should usually be warm, from 100° to 130° F. The ready removability of the silica by water, even though it contains sebum adsorbed thereon, makes it unnecessary at this stage to use washing ingredients such as synthetic detergents or soaps, to which a person might be allergic. Although the skin should be washed before the application of adsorbent if such adsorbent had not been previously used, this is not necessary when a new application of adsorbent is being made to replace that just removed. For daytime use, it will be possible to leave the adsorbent on the skin for up to 12 hours and it is preferably employed for from 6 to 10 hours. For nighttime use, it may be left on for from 6 to 12 hours.

Some of the advantages of the present invention have been indicated in the preceding description. Other desirable effects noted include maintenance of a non-oily skin without the need to employ chemical treatments of the skin, since the present methods are primarily physical in effect. Thus, it is not necessary to use hormones, radiation treatment, ultraviolet light, astringents or strong chemicals. Compounds such as astringents, which tighten the pores and diminish persiration, can also prevent the free flow of sebum to the surface, which flow should be maintained to keep from blocking the sebaceous ducts. The wicking effect of the silica promotes the flow of sebum and the maintenance of a healthy skin. The adsorption by the silica of the liquids helps to prevent oxidation and other chemical reactions thereof, with the concomitant development of malodorous or colored byproducts. It also prevents the sebum from discoloring make-up dyes and pigments and making them "orangey". Due to its finely divided form, the silica helps to cover skin blemishes and functions as a make-up base. These additional advantages are obtained without any diminution of the principal desired function of the silica, the maintenance of free sebum flow and non-oily appearing skin.

The following examples illustrate some aspects of the invention. They are not to be considered as limiting the scope of the invention since it is evident that they are only intended to be examplary thereof. Unless otherwise indicated, all temperatures are in degrees centigrade and all parts are by weight.

EXAMPLE 1

| | Parts by weight |
| --- | --- |
| Pyrogenic colloidal silica (Cab-O-Sil Type M-5) | 2.5 |
| Sodium carboxymethylcellulose | 0.5 |
| Glycerol | 1.0 |
| Water, deionized | 81.0 |
| Ethanol, denatured, SD 40 | 15.0 |

A liguid suspension of pyrogenic colloidal silica is prepared according to the above formula by blending the pyrogenic colloidal silica, dispersed in the water, into the alcohol-glycerine solvent mixture, in which the sodium carboxymethyl-cellulose has been dispersed. Mixings are effected at room temperature in a stainless steel vessel equipped with a variable speed propeller mixer. After blending together of the liguids, the stirring is continued for 15 minutes, after which time the liquid is satisfactorily thickened to a lotion-like consistency. In some cases, if the dispersion obtained is not considered to be satisfactory, additional stirring is employed and the product is put through a homogenizer.

After bottling and storage, which may be for a period of time up to a year or more, the pyrogenic colloidal silica is still in dispersion. If any has settled out or floated to the top of the product, it is dispersed by mere shaking or stirring.

In use, the product is applied at rates of from 0.002 to 0.08 grams per square centimeter to the faces of three males and three females, all of whom have what is commonly referred to as oily skin. On the average their facial skin excretes at least 0.7 milligrams of lipids per square centimeter per hour. Each person applies as much of the described suspension of pyrogenic colloidal silica as he or she considers desirable. The men use less of the product than the women because the women subsequently apply their regular make-up in customary fashion. Accordingly, the layers or pyrogenic colloidal silica desposited are only slightly noticeable on the skins of the men. The average rates of application of the above composition are about 0.002 to .03 g./sq. cm. for the men and about 0.2 to 0.08 g/sq. cm. for the women. The make-ups applied by the women contain F. D. & C. Yellow No. 5, F. D. & C. Red No. 3 and F. D. & C. Blue No. 1 as dyes and carmine lake, iron oxides, titanium dioxide as pigments, in addition to other usual facial make-up consituents.

Over a 6 hour period the facial skin of the users of these compositions is inspected for oiliness. It is found that the men's skins do not develop objectionable oiliness over this period of time and the women's skins are not oily. Make-ups are not discolored or made orangey. After passage of additional time, some excessive oil and perspiration appear, with the result that for the usual group of persons who have oily skin the present composition is considered to be useful for a period of from about 4 to 8 hours, before removal is desirable.

Removal of the absorbent from the skin is effected by washing with warm water at 120° F. Without the need for employing soaps or detergents. The sebum and oily material on the skin are removed with the pyrogenic colloidal silica as it is washed off, leaving the skin clean. More of the same composition is then applied so as to continue its sebrum absorbing action.

In a similar manner, a composition like that described above, but containing 8% pyrogenic colloidal silica, 3% sodium carboxymethylcellulose, 2% glycerine, 1% of a non-oily perfume, comprising principally known natural or synthetic perfumery ingredients soluble in alcohol, water or hydro-alcoholic solutions, 40% ethanol and 46% deionized water is applied to the subjects at approximately the same rates of total composition as are employed for the daytime product. This is kept on overnight, for a period of 8 to 11 hours, during which time it continues to absorb sebum and prevents the skin from becoming excessively oily.

Using different subjects, the daytime formula is applied to halves of the skins of the foreheads of a group of six adults, three male and three female, in sufficient quantity to deposit from 0.05 to 2.0 milligrams per square centimeter of the pyrogenic colloidal silica in smooth continuous films or layers. The amounts deposited are intentionally kept small enough so as not to be significantly obvious to an observer. The other halves of the foreheads are left untreated. Periodically, at times 4 to 8 hours after the application of the pyrogenic colloidal silica compositions, forehead prints are taken by pressing each side of the forehead of each user with an adsorbent tissue for a period of 3 seconds. The tissue is allowed to dry overnight, so as to permit volatiles from perspiration to evaporate off. The tissues are then observed. In each case, the tissue applied to the pyrogenic colloidal silica-treated forehead portion is signifi-cantly less oily than that applied to the untreated forehead surface. Such results are also obtained with the present compositions, into which there have been formulated minor proportions of bactericides, fungicides, dyes, pigments, inorganic thickening agents and exfoliants.

EXAMPLE 2

|  | Parts by weight |
|---|---|
| Pyrogenic colloidal silica (Cab-O-Sil Type M-5) | 2.0 |
| Veegum HV (thickening agent, made by R. T. Vanderbilt Co.) | 0.5 |
| Hydroxypropyl cellulose (Klusel NAP, made by Hercules Powder Corp.) | 1.0 |
| Chelating Agent (Chel DTPA, made by Geigy Corp.) | 0.025 |
| Hexachlorophene | 0.10 |
| F. D. & C. Blue dye No. 1, (1% aqueous solution) | 0.07 |
| F. D. & C. Yellow dye No. 5, (0.5% aqueous solution) | 0.12 |
| Water, deionized | 48.7 |
| 95% ethanol (SD 40) | 47.5 |

A liquid preparation for use as a sebum adsorbent is prepared by sifting the hydroxypropyl cellulose into a solution of the hexachlorophene in the alcohol over a period of about 60 minutes, after which the pyrogenic colloidal silica is stirred vigorously in about 30% of the water and the uniform mixture of pyrogenic colloidal silica in water is added to the hydroxypropyl cellulose-hexachlorophene-alcohol mixture, with stirring. The rest of the water for the formula is heated to a temperature of about 80° C. and the chelating agent and Veegum HV are added to it, with the Veegum being allowed to hydrate, after which the mixture is cooled to 25° C. The mixture of the other ingredients prepared is then stirred into the water-chelating agent-Veegum mixture and the dye solutions subsequently added, with stirring, until a uniform product results.

The cosmetic preparation made is bottled, distributed and used. In use, it is employed in a manner previously described with respect to the product of Example 1. In comparison with other allegedly useful sebum adsorbents, following the procedures previously given in Example 1, improved sebum adsorption is noted, which is considered to be especially important to the persons suffering from skin disorders in which the production of excess sebum accentuates the problems caused by the skin disorder. Thus, sebum production is decreased for acne sufferers and persons with oily skin and normal skins. The product is stable, pleasant to use, antibacterial and an effective adsorbent for oily products on the skin, such as sebum.

EXAMPLE 3

|  | Parts by weight |
|---|---|
| Pyrogenic colloidal silica (having an average particle diameter of about 11 millimicrons) | 2.0 |
| Hydroxypropyl cellulose | 1.0 |
| Ethanol | 48.0 |
| Hexachlorophene | 0.1 |
| Resorcinol | 0.2 |
| Veegum HV | 0.5 |
| F. D. & C. Blue dye No. 1 | 0.0008 |
| F. D. & C. Yellow dye No. 5 | 0.0006 |
| Water | 48.2 |

The product of the above formula is made in a manner similar to that described with respect to Example 2, with the resorcinol being added with the hexachlorophene to the alcohol. The product resulting, although it does not have the chelating properties given to the product of Example 2 by the Chel DTPA, when employed in the manner described with respect to the product of Example 1, is of similar good sebum adsorbent activity. When various changes are made in the proportions of the described ingredients or when they are replaced with equivalents, as taught in the specification, similar good effects are obtainable.

The invention has been described with respect to illustrative examples thereof. It will be clear that it is not to be limited to only those specific materials described since it will be evident to one of ordinary skill in the art that equivalents may be substituted for them without departing from the spirit of the invention or going outside the scope of the claims.

What is claimed is:

1. A method of slowing the development of oily skin which comprises applying to skin which normally becomes oily an oil-free suspension of pyrogenic colloidal silica in an aqueous-alcoholic medium, the particles of silica having at least 90% thereof with diameters between 2 and 20 millimicrons, said suspension containing from 0.5 to 10% by weight of the pyrogenic colloidal silica, 20 to 70% by weight water, 25 to 75% by weight of an aliphatic monohydric alcohol having from 2 to 4 carbon atoms, and 0.2 to 5% by weight of an organic thickening agent, said suspension being applied to the skin in a layer of a thickness corresponding to from $5 \times 10^{-5}$ to $1 \times 10^{-5}$ gram of silica per square centimeter of skin, said suspension being free of oil.

2. A composition for slowing the development of oily skin which consists essentially of an oil-free suspension of pyrogenic colloidal silica in an aqueous-alcoholic medium, the particles of silica having at least 90% thereof with diameters between 2 and 20 millimicrons, said suspension containing from 0.5 to 10% by weight of the pyrogenic colloidal silica, 20 to 70% by weight of water, 25 to 75% by weight of an aliphatic monohydric alcohol having from 2 to 4 carbon atoms, and 0.2 to 5% by weight of an organic thickening agent.

* * * * *